United States Patent
Chen et al.

(10) Patent No.: US 10,143,384 B2
(45) Date of Patent: Dec. 4, 2018

(54) SYSTEMS AND METHODS FOR ACCELERATED IMAGING USING VARIABLE DENSITY SAMPLING AND COMPRESSED SENSING WITH PARALLEL IMAGING

(71) Applicant: University of Virginia Patent Foundation, Charlottesville, VA (US)

(72) Inventors: Xiao Chen, Charlottesville, VA (US); Frederick H. Epstein, Charlottesville, VA (US); Yang Yang, Charlottesville, VA (US); Michael Salerno, Charlottesville, VA (US); Craig H. Meyer, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 744 days.

(21) Appl. No.: 14/677,905

(22) Filed: Apr. 2, 2015

(65) Prior Publication Data
US 2015/0285889 A1    Oct. 8, 2015

Related U.S. Application Data

(60) Provisional application No. 61/974,255, filed on Apr. 2, 2014.

(51) Int. Cl.
*G01V 3/00*    (2006.01)
*A61B 5/02*    (2006.01)
(Continued)

(52) U.S. Cl.
CPC .............. *A61B 5/02* (2013.01); *A61B 5/0044* (2013.01); *A61B 5/055* (2013.01);
(Continued)

(58) Field of Classification Search
CPC ................ G01R 33/4824; G01R 33/54; G01R 33/5611; G01R 33/56509; G01R 33/5635;
(Continued)

(56) References Cited

U.S. PATENT DOCUMENTS

2014/0219531 A1    8/2014    Epstein et al.
2015/0077112 A1*   3/2015    Otazo ................... A61B 5/055
                                                              324/318

OTHER PUBLICATIONS

Auger, D.A. et al., Semi-automated left ventricular segmentation based on a guide point model approach for 3D cine DENSE cardiovascular magnetic resonance, J Cardiovasc Magn Reson., 2014, pp. 1-12, 16(8).

(Continued)

*Primary Examiner* — Vinh Nguyen
(74) *Attorney, Agent, or Firm* — Meunier Carlin & Curfman LLC

(57) ABSTRACT

Some aspects of the present disclosure relate to accelerated imaging using variable-density sampling and compressed sensing with parallel imaging. In one embodiment, a method includes acquiring magnetic resonance data associated with a physiological activity in an area of interest of a subject. The acquiring includes performing accelerated variable-density sampling with phase-contrast displacement encoding. The method also includes reconstructing, from the acquired magnetic resonance data, images corresponding to the physiological activity in the area of interest. The reconstructing includes performing parallel imaging and compressed sensing.

18 Claims, 10 Drawing Sheets

(51) Int. Cl.
*A61B 5/055* (2006.01)
*G01R 33/561* (2006.01)
*G01R 33/48* (2006.01)
*G01R 33/54* (2006.01)
*G01R 33/56* (2006.01)
*A61B 5/00* (2006.01)

(52) U.S. Cl.
CPC ........ *G01R 33/5611* (2013.01); *A61B 5/0042* (2013.01); *G01R 33/4826* (2013.01); *G01R 33/546* (2013.01); *G01R 33/5608* (2013.01)

(58) Field of Classification Search
CPC ............ G01R 33/561; G01R 33/56383; G01R 33/5608; G01R 33/28; G01R 33/56375; G01R 33/5601; G01R 33/56308; G01R 33/5676; G01R 33/56316; G01R 33/56341; G01R 33/56; G01R 33/5614; G01R 33/563; G01R 33/5607; G01R 33/56545; G01R 33/446; G01R 33/4818; G01R 33/4822; G01R 33/4826; G01R 33/4835; G01R 33/485; G01R 33/56366; G01R 33/565; G01R 33/56527; G01R 33/56536; G01R 33/482; G01R 33/5619; G01R 33/546; G01R 33/5602; G01R 33/56333; A61B 5/004; A61B 5/0263; A61B 2576/023; A61B 5/0042; A61B 5/02; A61B 5/7425; A61B 6/503; A61B 6/5288; A61B 8/0883; A61B 8/5284; G06K 2209/05; G06K 9/6218

See application file for complete search history.

(56) References Cited

OTHER PUBLICATIONS

Candes, E.J. et al. "An Introduction to Compressive Sampling," IEEE Signal Processing Magazine, 2008, pp. 21-30, 25(2), IEEE.

Chen, X. et al., "Accelerated cine DENSE MRI using compressed sensing and parallel imaging," J Cardiovasc Magn Reson., Workshop Presentation, 2014, pp. 1-3, 16(Suppl 1):W16.

Chen, X. et al., "Motion-Compensated Compressed Sensing for Dynamic Contrast-Enhanced MRI Using Regional Spatiotemporal Sparsity and Region Tracking: Block LOw-rank Sparsity with Motion-guidance (BLOSM)," Magn Reson Med., 2014, pp. 1028-1038 72(4), Wiley Periodicals, Inc.

Clarke, G., "Parallel Imaging: Techniques, Quality Control, and Applications," Med. Phys., 2007, American Association of Physicists in Medicine, Annual Meeting 2007.

Fessler, J.A. et al., "Nonuniform Fast Fourier Transforms Using Min-Max Interpolation," IEEE Trans Med Imaging, 2003, pp. 560-574, 51(2), IEEE.

Pruessmann, K.P., et al., "SENSE: Sensitivity Encoding for Fast MRI," Magn Reson Med., 1999, pp. 952-962, 42(5), Wiley-Liss, Inc.

Simpson, R.M. et al., "MR assessment of regional myocardial mechanics," J Magn Reson Imaging, 2013, pp. 576-599, 37(3), Wiley Periodicals, Inc.

Spottiswoode, B.S. et al., Motion-Guided Segmentation for Cine DENSE MRI, Med Image Anal., 2009, pp. 105-115, 13(1).

Young, A.A. et al., "Generalized spatiotemporal myocardial strain analysis for DENSE and SPAMM imaging," Mag Reson Med., 2012, pp. 1590-1599, 67(6), Wiley-Liss, Inc.

Zhong, X. et al., "Imaging Three-Dimensional Myocardial Mechanics Using Navigator-gated Volumetric Spiral Cine DENSE MRI," Magn Reson Med., 2010, pp. 1089-1097, 64(4).

* cited by examiner

SYSTEMS AND METHODS FOR ACCELERATED IMAGING USING VARIABLE DENSITY SAMPLING AND COMPRESSED SENSING WITH PARALLEL IMAGING

CROSS-REFERENCE TO RELATED APPLICATION

This Application claims priority to and benefit under 35 U.S.C § 119(e) of U.S. Provisional Patent Application Ser. No. 61/974,255, entitled "Accelerated Cine DENSE using Variable Density Spirals and Compressed Sensing with Parallel Imaging," filed Apr. 2, 2014, which is hereby incorporated by reference herein in its entirety as if fully set forth below.

Some references, which may include patents, patent applications, and various publications, are cited in a reference list and discussed in the disclosure provided herein. The citation and/or discussion of such references is provided merely to clarify the description of the present disclosure and is not an admission that any such reference is "prior art" to any aspects of the present disclosure described herein. All references cited and discussed in this specification are incorporated herein by reference in their entireties and to the same extent as if each reference was individually incorporated by reference. In terms of notation, hereinafter, "[n]" represents the $n^{th}$ reference cited in the reference list. For example, [4] represents the $4^{th}$ reference cited in the reference list, namely, Candès, J. et al., "An Introduction to Compressive Sampling". IEEE Signal Processing Magazine, March 2008, p. 22.

STATEMENT REGARDING FEDERALLY SPONSORED RESEARCH

This invention was made with Government support under Grant Numbers R01 EB001763 and R01 HL115225, awarded by the National Institute of Health. The Government has certain rights in the invention.

BACKGROUND

The present disclosure generally relates to the field of medical imaging for analysis of certain physiological activities of a subject. Cardiac imaging to analyze myocardial strain, for example, is of growing importance for the clinical assessment of heart disease. Various conventional imaging techniques can provide for an assessment of the heart with regard to spatial coverage and an evaluation of the strain tensor. For example, three-dimensional (3D) measurements can provide a complete assessment of the heart with regard to spatial coverage and a comprehensive evaluation of the strain tensor.

Phase-contrast displacement encoding have been used for myocardial imaging, and cine DENSE (displacement encoding with stimulated echoes) has emerged as a strain imaging technique that, compared to tagging, can offer high spatial resolution, equivalent accuracy and better reproducibility, and where strain analysis is less time consuming. ([1], [2], [3]). DENSE can provide quantification of myocardial strain based on displacement of myocardial tissue, where tissue displacement is encoded as a phase of a stimulated-echo signal. Image acquisition times in cine DENSE can be relatively long and, due to properties inherent to stimulated echoes, signal-to-noise ratio (SNR) can be relatively low. The low SNR, requirements to preserve phase information, and cardiac motion present technical challenges.

It is with respect to these and other considerations that the various embodiments described below are presented.

SUMMARY

In one aspect, the present disclosure relates to a method for accelerated imaging of an area of interest of a subject. In one embodiment, the method includes acquiring magnetic resonance data associated with a physiological activity in an area of interest of a subject. The acquiring includes performing accelerated variable-density sampling with phase-contrast displacement encoding. The method also includes reconstructing, from the acquired magnetic resonance data, images corresponding to the physiological activity in the area of interest. The reconstructing includes performing parallel imaging and compressed sensing.

In another aspect, the present disclosure relates to a system for accelerated imaging of an area of interest of a subject. In one embodiment, the system includes a data acquisition device and an image processing device. The data acquisition device is configured to acquire magnetic resonance data associated with a physiological activity in an area of interest of a subject. The acquiring includes performing accelerated variable-density sampling with phase-contrast displacement encoding. The image processing device is configured to reconstruct, from the acquired magnetic resonance data, images corresponding to the physiological activity in the area of interest. The reconstructing includes performing parallel imaging and compressed sensing.

In yet another aspect, the present disclosure relates to a non-transitory computer-readable medium. In one embodiment, the computer-readable medium has stored computer-executable instructions that, when executed by one or more processors, cause a computer to perform a method for accelerated imaging of an area of interest of a subject. In one embodiment, the method includes acquiring magnetic resonance data associated with a physiological activity in an area of interest of a subject. The acquiring includes performing accelerated variable-density sampling with phase-contrast displacement encoding. The method also includes reconstructing, from the acquired magnetic resonance data, images corresponding to the physiological activity in the area of interest. The reconstructing includes performing parallel imaging and compressed sensing.

Other aspects and features according to the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

DETAILED DESCRIPTION

Figure 1:
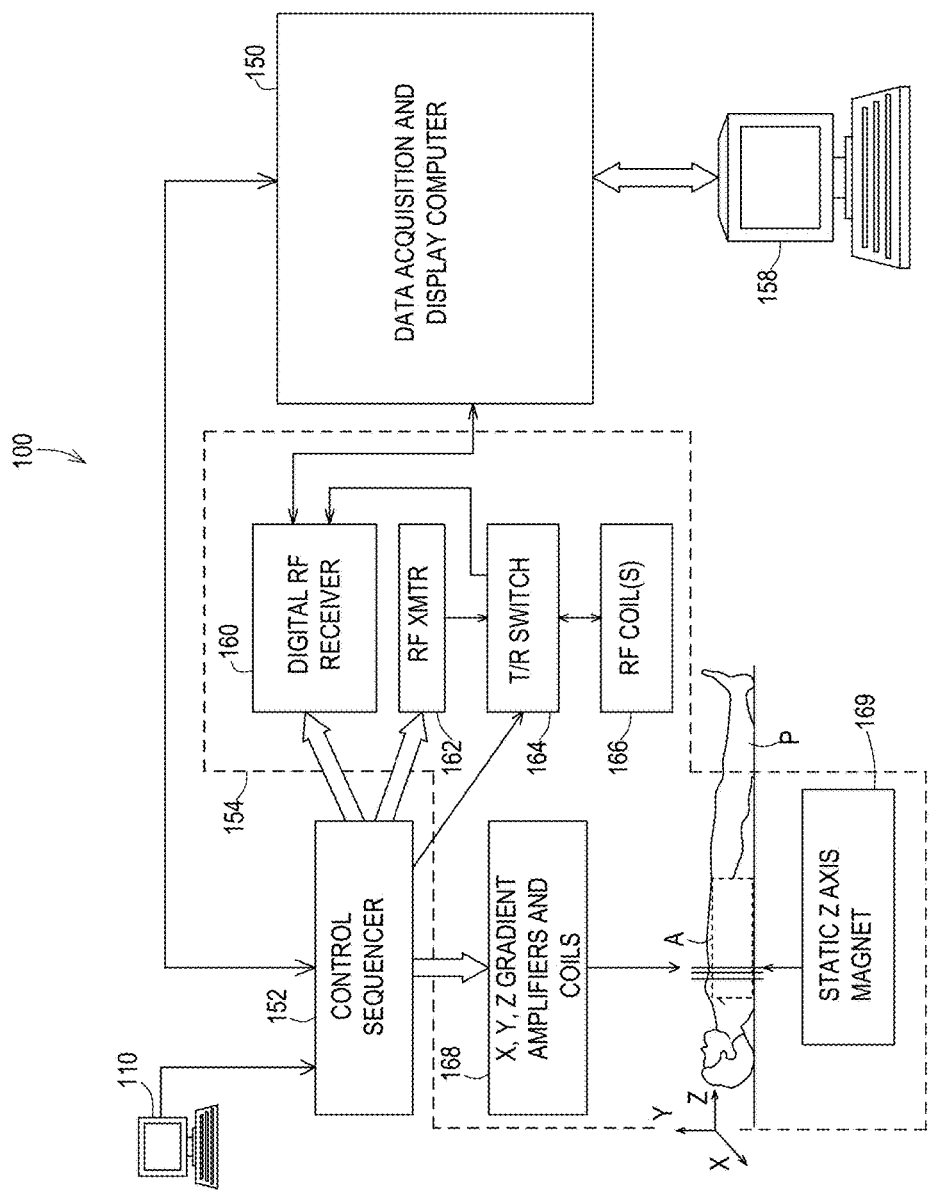
FIG. 1 is a system diagram illustrating an imaging system capable of implementing aspects of the present disclosure in accordance with one or more embodiments.

The present disclosure relates to methods, systems, and computer-readable media for performing aspects of accelerated imaging of an area of interest of a subject. Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise.

Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose.

It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

As discussed herein, a "subject" or "patient" may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g., rat, dog, pig, monkey), etc. It should be appreciated that the subject may be any applicable human patient, for example.

In the following description, references are made to the accompanying drawings that form a part hereof and that show, by way of illustration, specific embodiments or examples. In referring to the drawings, like numerals represent like elements throughout the several figures.

FIG. 1 is a system diagram illustrating an operating environment capable of implementing aspects of the present disclosure in accordance with one or more example embodiments. FIG. 1 illustrates an example of a magnetic resonance imaging (MRI) system 100, including a data acquisition and display computer 150 coupled to an operator console 110, an MRI real-time control sequencer 152, and an MRI subsystem 154. The MRI subsystem 154 may include XYZ magnetic gradient coils and associated amplifiers 168, a static Z-axis magnet 169, a digital RF transmitter 162, a digital RF receiver 160, a transmit/receive switch 164, and RF coil(s) 166. The MRI subsystem 154 may be controlled in real time by control sequencer 152 to generate magnetic and radio frequency fields that stimulate magnetic resonance phenomena in a living subject, patient P, to be imaged. A contrast-enhanced image of an area of interest A of the patient P may be shown on display 158. The display 158 may be implemented through a variety of output interfaces, including a monitor, printer, or data storage.

The area of interest A corresponds to a region associated with one or more physiological activities in patient P. The area of interest shown in the example embodiment of FIG. 1 corresponds to a chest region of patient P, but the area of interest for purposes of implementing aspects of the disclosure presented herein is not limited to the chest area. It should be recognized and appreciated that the area of interest can be one or more of a brain region, heart region, and upper or lower limb regions of the patient P, for example. Physiological activities that may be analyzed by methods and systems in accordance with various embodiments of the present disclosure may include, but are not limited to, muscular movement or fluid flow in particular areas of interest.

It should be appreciated that any number and type of computer-based medical imaging systems or components, including various types of commercially available medical imaging systems and components, may be used to practice certain aspects of the present disclosure. Systems as described herein with respect to example embodiments are not intended to be specifically limited to magnetic resonance imaging (MRI) implementations or the particular system shown in FIG. 1.

One or more data acquisition or data collection steps as described herein in accordance with one or more embodiments may include acquiring, collecting, receiving, or otherwise obtaining data such as imaging data corresponding to an area of interest. By way of example, data acquisition or collection may include acquiring data via a data acquisition device, receiving data from an on-site or off-site data acquisition device or from another data collection, storage, or processing device. Similarly, data acquisition or data collection devices of a system in accordance with one or more embodiments of the present disclosure may include any device configured to acquire, collect, or otherwise obtain data, or to receive data from a data acquisition device within the system, an independent data acquisition device located on-site or off-site, or another data collection, storage, or processing device.

Figure 2:
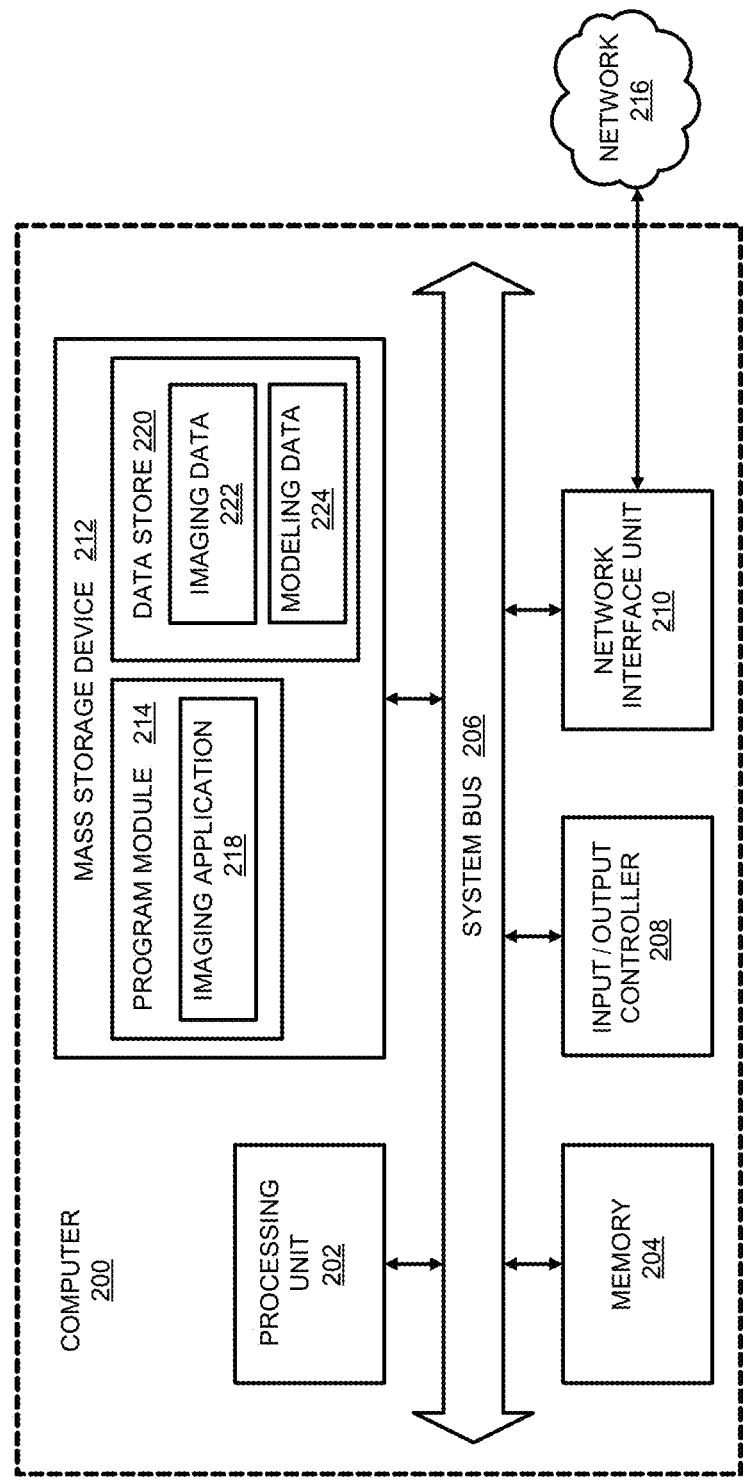
FIG. 2 is a computer architecture diagram showing a general computing system capable of implementing aspects of the present disclosure in accordance with one or more embodiments.

FIG. 2 is a computer architecture diagram showing a general computing system capable of implementing aspects of the present disclosure in accordance with one or more embodiments described herein. A computer 200 may be configured to perform one or more functions associated with embodiments illustrated in one or more of FIGS. 3-10. For example, the computer 200 may be configured to perform operations of the method shown in FIG. 3 and as described below. It should be appreciated that the computer 200 may be implemented within a single computing device or a computing system formed with multiple connected computing devices. The computer 200 may be configured to perform various distributed computing tasks, which may distribute processing and/or storage resources among the multiple devices. The data acquisition and display computer 150 and/or operator console 110 of the system shown in FIG. 1 may include one or more systems and components of the computer 200.

As shown, the computer 200 includes a processing unit 202 ("CPU"), a system memory 204, and a system bus 206 that couples the memory 204 to the CPU 202. The computer 200 further includes a mass storage device 212 for storing program modules 214. The program modules 214 may be operable to perform one or more functions associated with embodiments illustrated in one or more of FIGS. 3-10 discussed below, for example to cause the computer 200 to perform operations of the method shown in FIG. 3 and as described below. The program modules 214 may include an imaging application 218 for performing data acquisition functions as described herein, for example to receive image data corresponding to magnetic resonance imaging of an area of interest. The computer 200 can include a data store 220 for storing data that may include imaging-related data 222 such as acquired image data, and a modeling data store 224 for storing image modeling data, or other various types of data utilized in practicing aspects of the present disclosure.

The mass storage device 212 is connected to the CPU 202 through a mass storage controller (not shown) connected to the bus 206. The mass storage device 212 and its associated computer-storage media provide non-volatile storage for the computer 200. Although the description of computer-storage media contained herein refers to a mass storage device, such as a hard disk or CD-ROM drive, it should be appreciated by those skilled in the art that computer-storage media can be any available computer storage media that can be accessed by the computer 200.

By way of example, and not limitation, computer-storage media (also referred to herein as a "computer-readable storage medium" or "computer-readable storage media") may include volatile and non-volatile, removable and non-removable media implemented in any method or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 200. Transitory signals are not "computer-storage media", "computer-readable storage medium" or "computer-readable storage media" as described herein.

According to various embodiments, the computer 200 may operate in a networked environment using connections to other local or remote computers through a network 216 via a network interface unit 210 connected to the bus 206. The network interface unit 210 may facilitate connection of the computing device inputs and outputs to one or more suitable networks and/or connections such as a local area network (LAN), a wide area network (WAN), the Internet, a cellular network, a radio frequency network, a Bluetooth-enabled network, a Wi-Fi enabled network, a satellite-based network, or other wired and/or wireless networks for communication with external devices and/or systems. The computer 200 may also include an input/output controller 208 for receiving and processing input from a number of input devices. Input devices may include one or more of keyboards, mice, stylus, touchscreens, microphones, audio capturing devices, or image/video capturing devices. An end user may utilize such input devices to interact with a user interface, for example a graphical user interface, for managing various functions performed by the computer 200.

The bus 206 may enable the processing unit 202 to read code and/or data to/from the mass storage device 212 or other computer-storage media. The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology. The computer-storage media may also represent secondary storage, whether implemented as hard drives or otherwise. Hard drive implementations may be characterized as solid state, or may include rotating media storing magnetically-encoded information. The program modules 214, which include the imaging application 218, may include instructions that, when loaded into the processing unit 202 and executed, cause the computer 200 to provide functions associated with embodiments illustrated in FIGS. 3-10. The program modules 214 may also provide various tools or techniques by which the computer 200 may participate within the overall systems or operating environments using the components, flows, and data structures discussed throughout this description.

In general, the program modules 214 may, when loaded into the processing unit 202 and executed, transform the processing unit 202 and the overall computer 200 from a general-purpose computing system into a special-purpose computing system. The processing unit 202 may be constructed from any number of transistors or other discrete circuit elements, which may individually or collectively assume any number of states. More specifically, the processing unit 202 may operate as a finite-state machine, in response to executable instructions contained within the program modules 214. These computer-executable instructions may transform the processing unit 202 by specifying how the processing unit 202 transitions between states, thereby transforming the transistors or other discrete hardware elements constituting the processing unit 202.

Encoding the program modules 214 may also transform the physical structure of the computer-storage media. The specific transformation of physical structure may depend on various factors, in different implementations of this description. Examples of such factors may include, but are not limited to the technology used to implement the computer-storage media, whether the computer storage media are characterized as primary or secondary storage, and the like. For example, if the computer-storage media are implemented as semiconductor-based memory, the program modules 214 may transform the physical state of the semiconductor memory, when the software is encoded therein. For example, the program modules 214 may transform the state of transistors, capacitors, or other discrete circuit elements constituting the semiconductor memory.

As another example, the computer-storage media may be implemented using magnetic or optical technology. In such implementations, the program modules 214 may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. Other transformations of physical media are possible without departing from the scope of the present description, with the foregoing examples provided only to facilitate this discussion.

Figure 3:
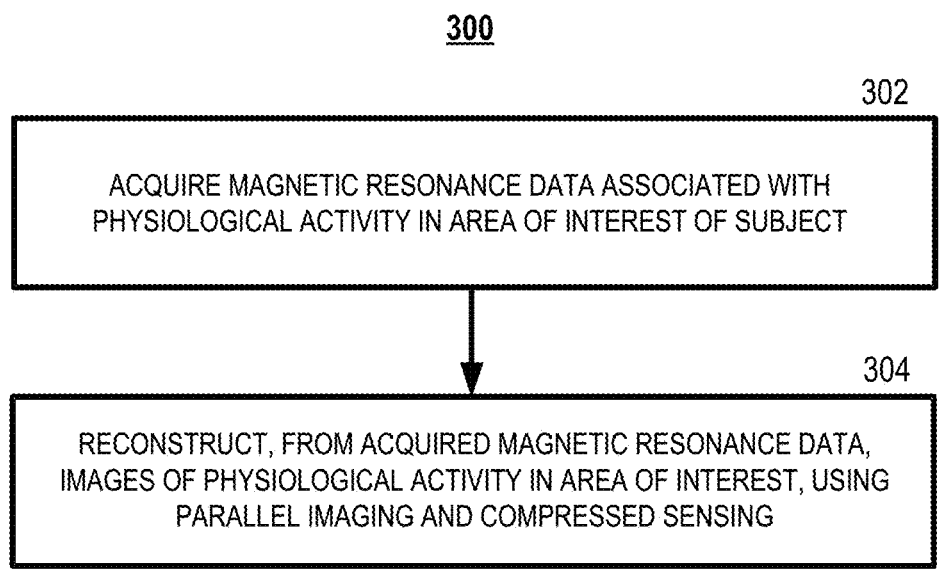
FIG. 3 is a flow diagram illustrating operations of a method for accelerated imaging of an area of interest of a subject, according to one embodiment of the present disclosure.

FIG. 3 is a flow diagram illustrating operations of a method 300 for accelerated imaging of an area of interest of a subject, according to one embodiment of the present disclosure. As shown, the method 300 includes operation 302, where magnetic resonance data associated with a physiological activity in an area of interest of a subject is acquired. The acquiring of the magnetic resonance data at operation 302 includes performing accelerated variable-density sampling with phase-contrast displacement encoding. The method 300 also includes operation 304, where images corresponding to the physiological activity in the area of interest are reconstructed from the acquired magnetic resonance data. The reconstructing of the images at operation 304 includes performing parallel imaging and compressed sensing.

The variable-density sampling may include variable-density spiral sampling, and the phase-contrast displacement encoding may include cine displacement encoding with stimulated echoes (DENSE). The acquiring of the magnetic resonance data may use a variable density Cartesian trajectory or a non-Cartesian trajectory.

The parallel imaging may include combining multi-channel parallel imaging data using sensitivity maps calculated from temporally-averaged data. The compressed sensing may include regional-sparsity based compressed sensing. The compressed sensing may include regional-sparsity based compressed sensing and motion-guided compressed sensing wherein: combined images from the parallel imaging are divided into regions; each of the regions is motion-tracked over time; and, matrix low-rank sparsity is exploited in the motion-tracked regions to remove artifacts. The compressed sensing may alternatively include regional-sparsity based compressed sensing wherein combined images from the parallel imaging are divided into regions, and the regions are treated as static over time and low-rank sparsity is exploited in the same image region over time.

Performing the accelerated variable-density sampling with phase-contrast displacement encoding may include spiral sampling with fully-sampled or over-sampled center portions of the k-space and undersampled outer portions of the k-space. Undersampling may be performed in the in-plane $k_x$-$k_y$ direction, and for three-dimensional imaging, undersampling may be performed in the through-plane $k_z$ direction, which may include fully sampling center $k_z$ partitions and randomly sampling higher spatial frequency $k_z$ partitions.

The compressed sensing may include performing motion-guided compressed sensing functions wherein three-dimensional images from the parallel imaging are divided into cubes that are motion-tracked over time and low-rank sparsity is exploited inside the motion-tracked cubes to remove artifacts. Alternatively, the cubes may be treated as static over time and low-rank sparsity may be exploited in the same cube over time.

The method 300 may also include identifying, based on the reconstructed images, one or more characteristics of the physiological activity in the area of interest of the subject. The area of interest of the subject may include the heart of the subject, and the one or more characteristics of the physiological activity may include myocardial strain. The variable-density sampling may comprise variable-density spiral sampling that includes distributing spiral interleaves uniformly within each of a plurality of cardiac phases and rotation by the golden angle through different cardiac phases of the plurality of cardiac phases.

The following description provides a further discussion of certain aspects of the present disclosure in accordance with example embodiments. A discussion of example implementations and results of practicing various aspects of the present disclosure will also be presented.

In some embodiments of the present disclosure, a cine DENSE pulse sequence is used to achieve acceleration, with compressed sensing (CS) and parallel imaging (PI). Those skilled in the art will recognize that compressed sensing generally refers to a signal processing technique for efficiently recovering certain signals and images, which relies on principles of sparsity and incoherence. ([4]). Those skilled in the art will also recognize that in the context of magnetic resonance imaging, parallel imaging generally refers to methods that use spatial information obtained from arrays of RF coils sampling data in parallel. ([5]).

In some embodiments of the present disclosure, variable-density spiral sampling is used for data acquisition, with full sampling for the center of k-space and undersampling for the outer portion of k-space. Spiral interleaves (see FIG. 4) can be uniformly distributed within each cardiac phase and rotated by the golden angle through different cardiac phases to achieve randomness in time.

Figure 5:
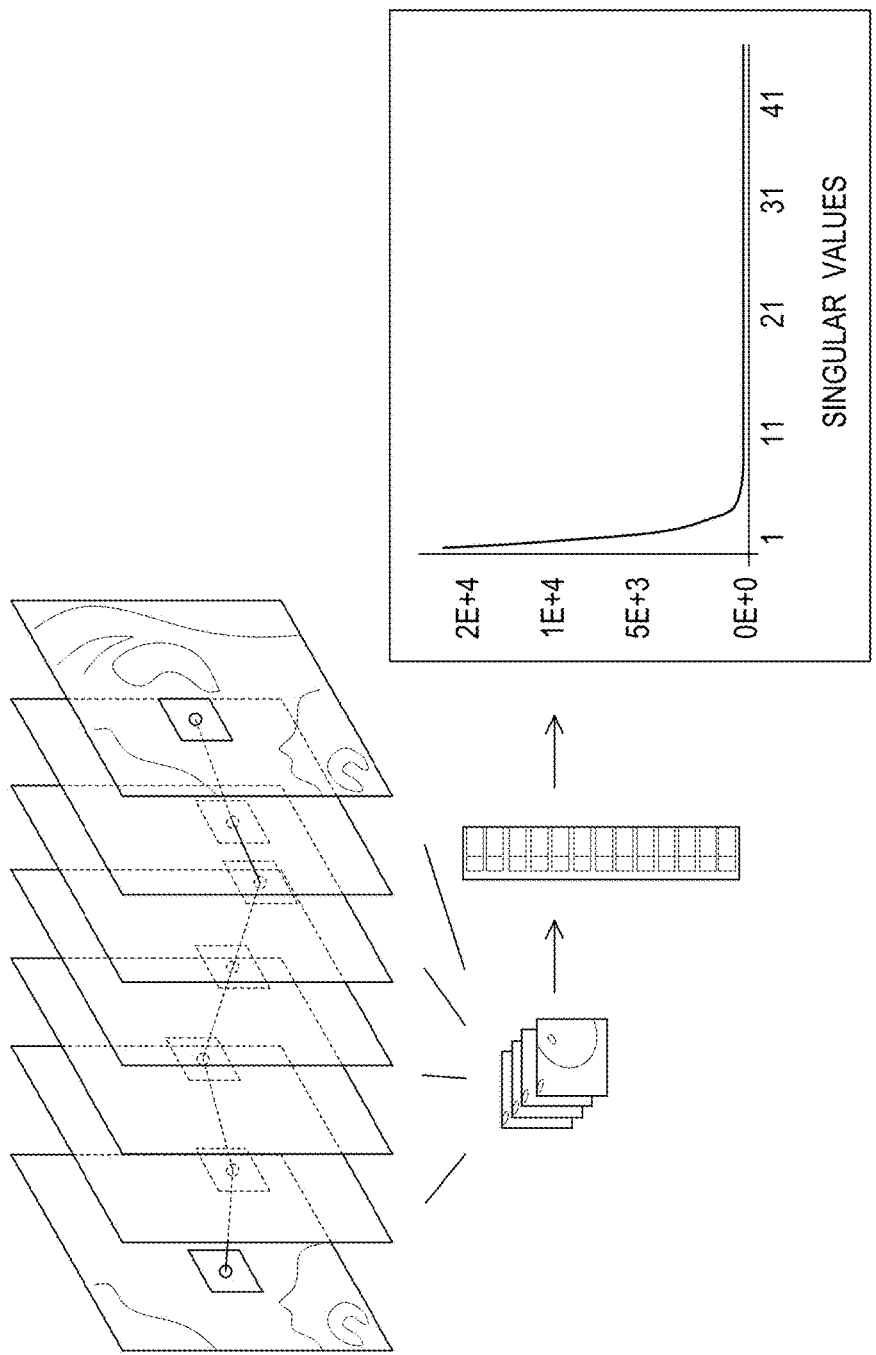
FIG. 5 illustrates aspects of compressed sensing using 2D BLOSM in accordance with one embodiment of the present disclosure.

In some embodiments, image reconstruction is performed using a Block LOw-rank Sparsity with Motion-guidance (BLOSM) CS method ([6],[7]) combined with sensitivity encoding (SENSE) ([8]). SENSE is based on the fact that receiver sensitivity generally has an encoding effect complementary to Fourier preparation by linear field gradients. Thus, by using multiple receiver coils in parallel scan time in Fourier imaging can be considerably reduced. This approach exploits matrix low-rank sparsity within motion-tracked regions of SENSE-combined images. As shown in FIG. 5, after the multi-channel data are combined with SENSE, regions (blocks) are initialized on the first image. Each block is motion-tracked to the succeeding images through time using motion trajectories from image registration. The blocks are gathered into a 3D cluster and further rearranged into a 2D matrix with high spatial-temporal correlations. The sparsity is exploited using singular value decomposition.

Sensitivity maps can be calculated from temporally-averaged DENSE phase reference data to avoid phase aliasing when estimating coil sensitivities. Non-uniform fast-Fourier Transform (FFT) ([9]) can be used for transforming data between k-space and the image domain.

In some embodiments of the present disclosure, three-dimensional (3D) cine DENSE is used to achieve acceleration using compressed sensing (CS) and parallel imaging (PI). The 3D cine DENSE technique may be a modified version of a navigator-gated 3D spiral cine DENSE sequence ([10]). In some embodiments, data undersampling can be performed both in the in-plane ($k_x$-$k_y$) and through-plane ($k_z$) directions. For in-plane acceleration, a select number of variable-density spiral interleaves can be used in accordance with a predetermined rate of acceleration. The interleaves can be uniformly distributed within each cardiac phase and rotated by the golden angle through different cardiac phases. For through-plane acceleration, a select number of partition encodings, according to a predetermined rate of acceleration, can be acquired following a variable density $k_z$-t sampling pattern wherein a predetermined number of center $k_z$ partitions are fully sampled and higher spatial frequency $k_z$ partitions are randomly sampled.

In some embodiments, image reconstruction and analysis uses BLOSM and SENSE in which certain techniques used for reconstructed accelerated two-dimensional (2D) cine DENSE imaging ([11]) are extended for use in 3D imaging (3D BLOSM-SENSE). In the extended technique for 3D imaging, multi-channel data can be combined into images using sensitivity maps calculated from temporally-averaged data. The dynamic 3D images can be divided into small cubes and matrix low rank sparsity can be exploited inside these cubes to remove artifacts.

As shown in FIG. 5, in 2D BLOSM, images may be divided (separated) into regions, the regions may be tracked over time, and singular value decomposition (SVD) may be applied to the tracked regions, which can both account for regional non-periodic variations in motion and can exploit regional spatiotemporal sparsity. ([6], [7]). In some embodiments, the regions may be square blocks, and aspects of matrix low-rank sparsity are utilized. BLOSM can utilize data-driven spatiotemporal basis functions applied to regions and achieve motion compensation by embedding regional motion tracking into the iterative compressed sensing (CS) image reconstruction algorithm. With this combination, BLOSM can attain benefits of data-driven spatiotemporal basis functions while substantially reducing artifacts from non-periodic motion such as breathing.

Figure 4:
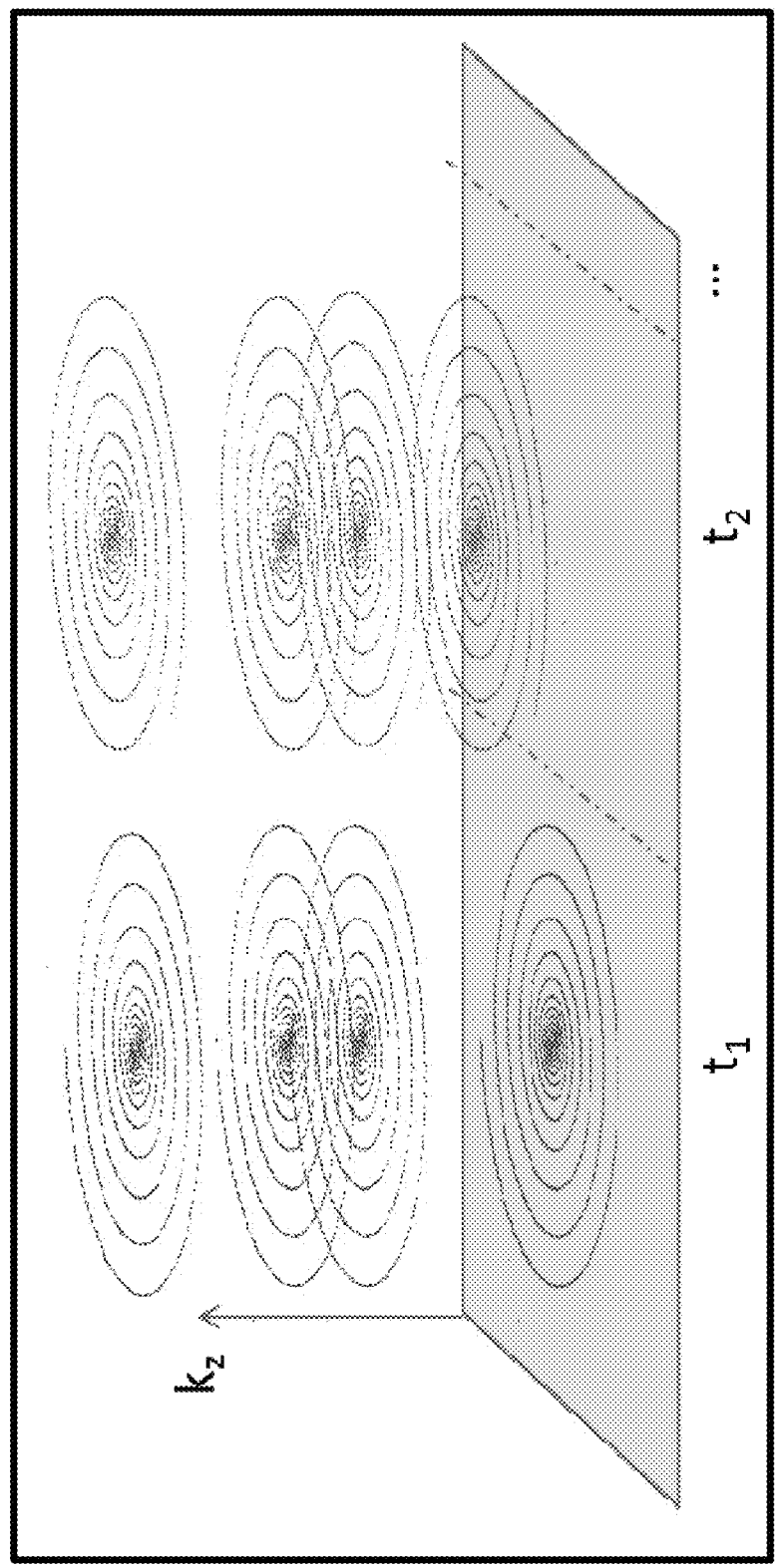
FIG. 4 illustrates spiral interleaves used in data acquisition in accordance with one embodiment of the present disclosure.

In some embodiments of the present disclosure, accelerated three-dimensional (3D) cine DENSE is achieved using compressed sensing (CS) and parallel imaging (PI). The 3D cine DENSE technique may be a modified version of a navigator-gated 3D spiral cine DENSE sequence ([10]). In some embodiments, stack-of-spirals trajectory is used to cover the 3D k-space and data undersampling can be performed both in the in-plane ($k_x$-$k_y$) and through-plane ($k_z$) directions. For in-plane acceleration, a select number of variable-density spiral interleaves can be used in accordance with a predetermined rate of acceleration. In FIG. 4, one spiral interleaf is acquired for each partition ($k_z$). If more than one interleaf is acquired for each partition, the in-plane interleaves can be uniformly distributed within each cardiac phase. For through-plane acceleration, a select number of partition encodings, according to a predetermined rate of acceleration, can be acquired following a variable density $k_z$-t sampling pattern wherein a predetermined number or percentage of center $k_z$ partitions are fully sampled for all time points (see $t_1$ and $t_2$ in FIG. 4) and higher spatial frequency $k_z$ partitions are randomly sampled. In some embodiments, the in-plane spiral interleaves are rotated by the golden angle through different time points (cardiac phases). In some embodiments, the in-plane spiral interleaves are rotated by the golden angle through different time points and different $k_z$ encoding.

In some embodiments, image reconstruction uses a combination of BLOSM and SENSE in which certain techniques used for reconstructed accelerated two-dimensional (2D) cine DENSE imaging ([11]) are extended for use in 3D imaging (3D BLOSM). In the extended technique for 3D imaging, multi-channel data can be combined into single-channel images using 3D sensitivity maps calculated from temporally-averaged data. The dynamic 3D images can be divided into small cubes and matrix low rank sparsity can be exploited inside these cubes to remove artifacts.

In the BLOSM technique ([6], [7]), images may be divided (separated) into regions, the regions may be tracked over time, and singular value decomposition (SVD) may be applied to the tracked regions, which can both account for regional non-periodic variations in motion and can exploit regional spatiotemporal sparsity. In some example embodiments, the regions may be square blocks, and aspects of matrix low-rank sparsity are utilized. BLOSM can utilize data-driven spatiotemporal basis functions applied to regions and achieve motion compensation by embedding regional motion tracking into the iterative compressed sensing (CS) image reconstruction algorithm. With this combination, BLOSM can attain benefits of data-driven spatiotemporal basis functions while substantially reducing artifacts from non-periodic motion such as breathing.

Some aspects of tracking blocks of pixels and exploiting regional low-rank sparsity using BLOSM will now be described. As described in further detail in U.S. Patent Pub. No. 2014/0219531, in implementations of BLOSM, block of pixels can be tracked throughout frames. Temporally related blocks with similar spatial contents are gathered together to form a 3D ($N_b \times N_b \times N_t$) cluster, the content of which has a high spatiotemporal correlation. The cluster is rearranged into a 2D matrix ($N_s \times N_t$, $N_s = N_b \times N_b$), and Singular value decomposition (SVD) is applied to the matrix. The smaller singular values which mainly represent noises and artifacts are diminished, while the larger singular values which mainly represent the real object are kept.

Figure 6:
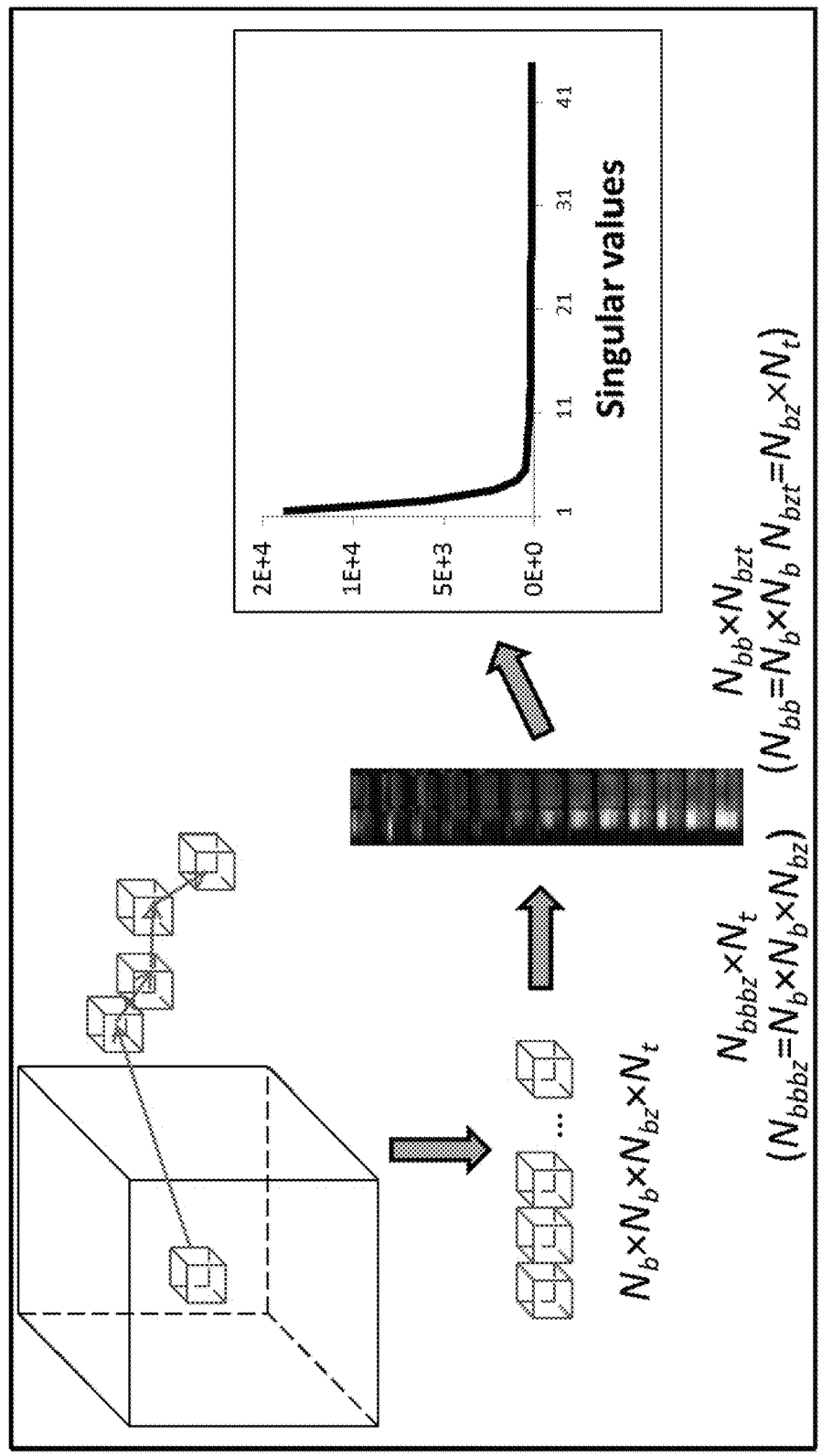
FIG. 6 illustrates aspects of compressed sensing using 3D BLOSM in accordance with one embodiment of the present disclosure.

Now also referring to FIG. 6, in some embodiments of the present disclosure, image reconstruction and analysis uses BLOSM and SENSE in which certain techniques for reconstructed accelerated 2D cine DENSE imaging are extended for use in 3D imaging (3D BLOSM). In the extended technique for 3D imaging, multi-channel data can be combined into images using 3D sensitivity maps calculated from temporally-averaged data. In 3D BLOSM according to some embodiments of the present disclosure, dynamic 3D images combined using SENSE can be divided into small cubes. The cubes are motion tracked through time for all the time points and are then gathered together into a 4D cluster, containing highly spatial and temporal correlated 3D imaging contents. The correlation can be exploited using matrix low rank sparsity in these cubes to remove artifacts.

As illustrated in FIG. 6, in 3D BLOSM, a 3D image x×y×z is obtained for each point in time and a 3D cube of size $N_b \times N_b \times N_{bz}$ is tracked at each time point for each 3D image. Thus, a four-dimensional (4D) dataset is obtained, with size of $N_b \times N_b \times N_{bz} \times t$. In order to convert the 4D dataset into a 2D matrix for SVD analysis, x, y, and z can be placed in one dimension and time t can be placed in another dimension, such that the 2D matrix $N_{bbbz}$ by t, where $N_{bbbz}=N_b \times N_b \times N_{bz}$. Alternatively, x and y can be placed in one dimension and z and t placed in the other dimension, such that the 2D matrix for SVD analysis is $N_{bb}$ by $N_{bzt}$, where $N_{bb}=N_b \times N_b$ and $N_{bzt}=N_{bz} \times t$. Thresholding operations can be performed in singular values to get rid of small singular values that may represent noise or artifacts. The filtered 2D matrix can then be converted back into a group of cubes. The cubes can be put back into the larger 4D image, which is the full 3D image and time. An average can be used to allow for any overlapping of the cubes. Once the whole image is obtained, compensation for the data fidelity in the 4D image can be performed, thus completing one iteration of the 3D BLOSM process. Multiple iterations can be performed until a predetermined condition is satisfied, for instance a predetermined number of iterations, predetermined period of time, and/or predetermined convergence level.

In alternative embodiments of compressed sensing according to the present disclosure, rather than tracking motion for each of the cubes over time, the cubes can be treated to be static over time and low-rank sparsity is exploited in the same cube over time. Approaches other than the above-described technique can be used for converting a 4D dataset to a 2D matrix for SVD to get the singular values. Further, higher-order singular value decomposition functions (HOSVD) may be used in order to analyze a higher dimensional matrix. Also, in 3D cine DENSE according to one or more embodiments disclosed herein, joint-sparsity reconstruction can be performed, where data from different displacement encodings are put together for reconstruction.

EXAMPLE IMPLEMENTATIONS AND RESULTS

The following describes examples of implementing some aspects of the present disclosure, and corresponding results.

Example 1

A first example (Example 1) of practicing aspects of the present disclosure will now be described, along with corresponding results. Example 1 shows an implementation of accelerated cine DENSE MRI techniques with image reconstruction using compressed sensing (CS) and parallel imaging (PI).

Methods

A variable-density spiral cine DENSE sequence was implemented where the center of k-space was fully sampled and the outer portion of k-space was undersampled. Spiral interleaves were distributed uniformly within each cardiac phase and rotated by the golden angle through different cardiac phases to achieve randomness in time. For image reconstruction, BLOSM was used for compressed sensing, combined with parallel imaging using SENSE. This approach exploits matrix low-rank sparsity within motion-tracked regions of SENSE-combined images. Sensitivity maps were calculated from temporally-averaged DENSE phase reference data to avoid phase aliasing when estimating coil sensitivities. Non-uniform FFT ([9]) was used for transforming data between k-space and the image domain. For comparison, undersampled datasets were also reconstructed using SENSE without CS.

Short-axis cine DENSE images of the left ventricle were collected from 5 healthy volunteers on a 1.5 T MRI scanner (Siemens Avanto) with a body-spine combined array RF coil (5 channel). Fully-sampled datasets with 2D in-plane displacement encoding and 6 to 8 spiral interleaves per image were acquired within a long breathhold (20 to 26 heartbeats), and prospectively accelerated datasets at rates 2 and 4 (with 4 and 2 spiral interleaves per image) were acquired within much shorter breathholds of 14 and 8 heartbeats, respectively. The fully-sampled datasets provided reference images, and retrospective undersampling of these datasets was used to evaluate the new methodologies. Prospectively acquired undersampled cine DENSE datasets demonstrated true acceleration. Imaging parameters included field of view (FOV) 280-320×280-320 mm$^2$, spatial resolution 1.8-2.2× 1.8-2.2×8 mm$^3$, ramped flip angle with the last flip angle=15°, TR 9.8 ms, TE 1.3 ms, temporal resolution 19.6 ms, and cardiac phases 35-38. Image quality was analyzed by measuring the mean squared error (MSE) for retrospectively undersampled data and the SNR for all the data. Myocardial strain was computed using standard methods ([2]). Using the retrospectively undersampled and prospectively accelerated data, segmental circumferential stain ($E_{cc}$) was compared to the fully-sampled data.

Results

Figure 7:
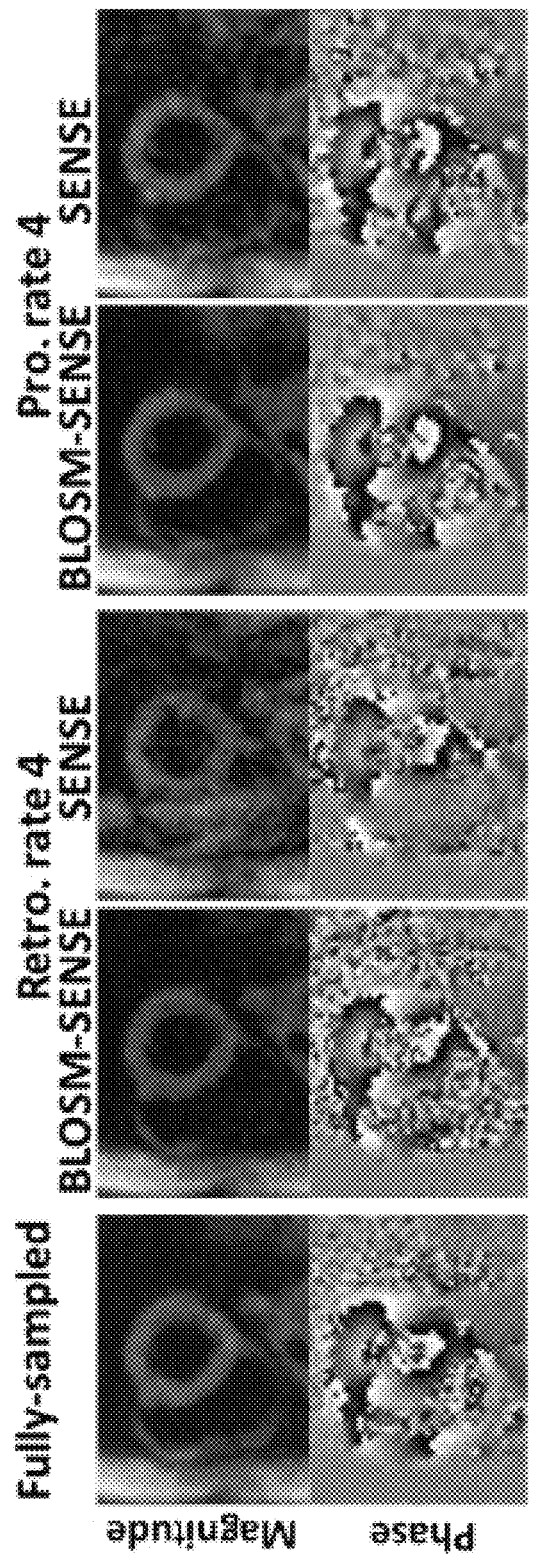
FIG. 7 shows end-systolic DENSE images, with magnitude and phase-reconstructed images from fully-sampled, retrospectively undersampled, and prospectively accelerated datasets. BLOSM-SENSE and SENSE reconstructions are shown.
Figure 8:
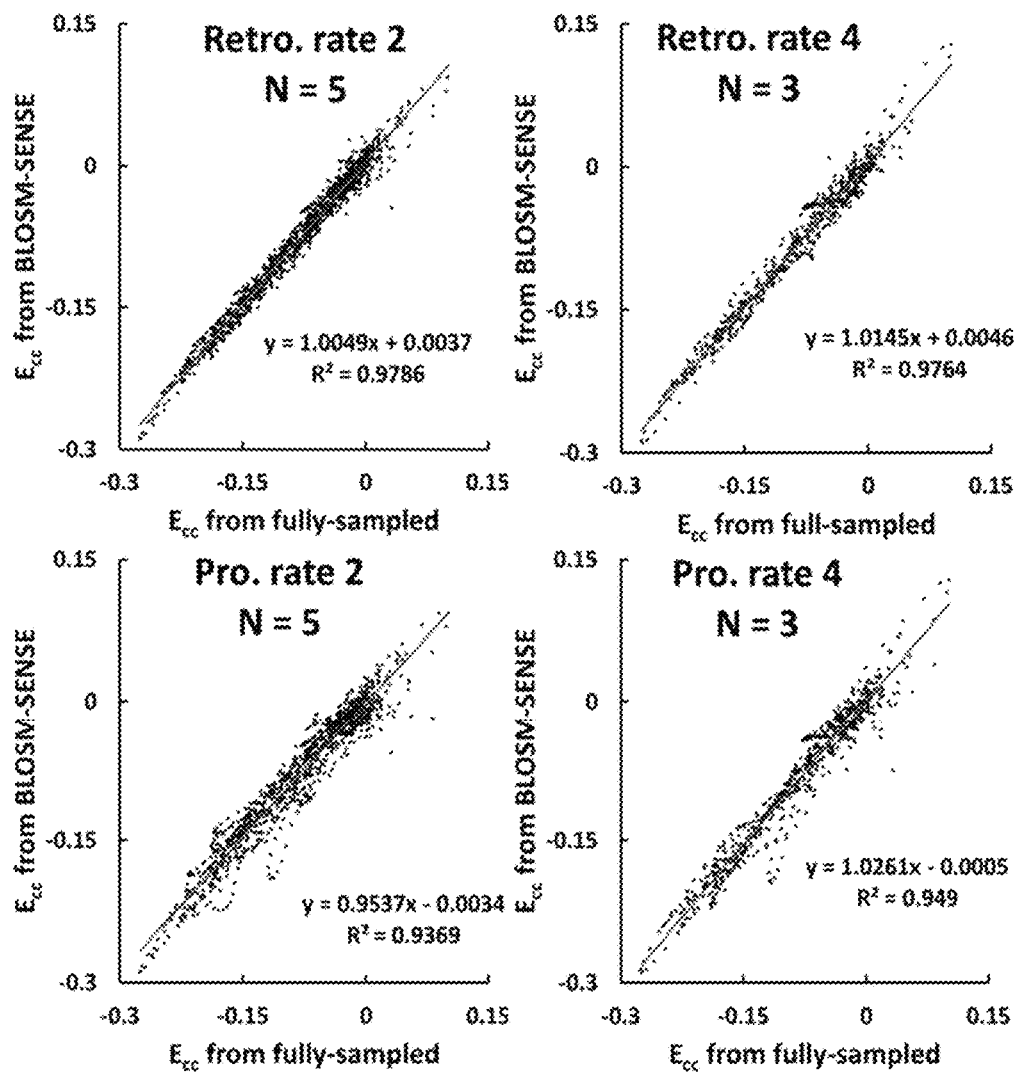
FIG. 8 shows correlation of segmental $E_{cc}$ from retrospectively undersampled and prospectively accelerated cine DENSE versus fully-sampled data.

FIG. 7 shows resulting end-systolic DENSE images, with magnitude and phase-reconstructed images from fully-sampled, retrospectively undersampled, and prospectively accelerated datasets. BLOSM-SENSE and SENSE reconstructions are shown. For the 5 volunteers, Retro. rate 2 BLOSM-SENSE MSE=1.5±0.4e-7, SENSE 3.9±0.5e-7; Retro. rate 4 BLOSM-SENSE MSE=1.5±0.5e-7, SENSE 7.1±1e-7. Also, for the 5 volunteers, fully-sampled SNR=23.9±4.2, rate 4 BLOSM-SENSE 18.1±7.4, SENSE 6.9±3.1; ANOVA P<0.01 BLOSM-SENSE vs. SENSE. Images reconstructed with BLOSM-SENSE had lower error and higher SNR than using SENSE alone (p<0.01). As illustrated in FIG. 8, $E_{cc}$ computed from BLOSM-SENSE-reconstructed undersampled data from all 5 volunteers correlated closely with fully sampled data for both rates 2 and 4, and for both retrospectively and prospectively accelerated data.

Thus, it is shown by the results in the implementation of aspects of the present disclosure in this Example 1 that using variable-density spiral acquisitions with golden angle rotations and BLOSM-SENSE reconstruction, accelerated cine DENSE images with two-dimensional in-plane displacement encoding can be acquired in a single breathhold, as short as 8 heartbeats. This represents an improvement over prior protocols that may require two 14-heartbeats breathholds or more to acquire equivalent datasets. These methods, when available with rapid online reconstruction, may significantly simplify the clinical use of cine DENSE for high-quality myocardial strain imaging.

Example 2

A second example (Example 2) of practicing aspects of the present disclosure will now be described, along with corresponding results. Example 2 shows an implementation of three-dimensional (3D) cine DENSE used to achieve acceleration using compressed sensing (CS) and parallel imaging (PI). The 3D cine DENSE technique may be a modified version of a navigator-gated 3D spiral cine DENSE sequence ([4]).

Methods

A navigator-gated 3D stack-of-spirals cine DENSE sequence ([4]) was modified to achieve acceleration using compressed sensing and parallel imaging (CS-PI). Data undersampling was performed both in the in-plane ($k_x$-$k_y$) and through-plane ($k_z$) directions. For in-plane acceleration, 2 out of 6 variable-density spiral interleaves were used (rate-3 acceleration). The 2 spiral interleaves were uniformly distributed within each cardiac phase and rotated by the golden angle through different cardiac phases. For through-plane acceleration, 7 out of 14 partition encodings (rate-2 acceleration) were acquired following a variable density $k_z$-t sampling pattern where the center 3 $k_z$ partitions were fully sampled and higher spatial frequency kz partitions were randomly sampled.

For data collection, prospectively rate-6 (3×2) accelerated 3D cine DENSE data were collected from 6 healthy volunteers on a 1.5 T scanner (Siemens Avanto) using a 5-channel RF coil. The imaging protocol included: voxel size ~2.5× 2.5×5.0 mm3, temporal resolution 32 msec, cardiac phases ~22, displacement-encoding frequency $k_e$=0.06 cycles/mm, end expiration navigator acceptance window width of ±3 mm. Fully-sampled 3D cine DENSE scans were also completed for 4 cases. Two scans were not completed due to drifting respiratory patterns.

For data reconstruction and analysis, a CS BLOSM and SENSE technique was used for reconstruction of accelerated 2D cine DENSE imaging. This technique was extended for 3D imaging (3D BLOSM-SENSE). Multi-channel data were combined into images using sensitivity maps calculated from temporally-averaged data. The dynamic 3D images were divided into small cubes and matrix low rank sparsity was exploited inside these cubes to remove artifacts. Three-dimensional strain analyses were performed using a semi-automatic method ([12]).

Results

Figure 9:
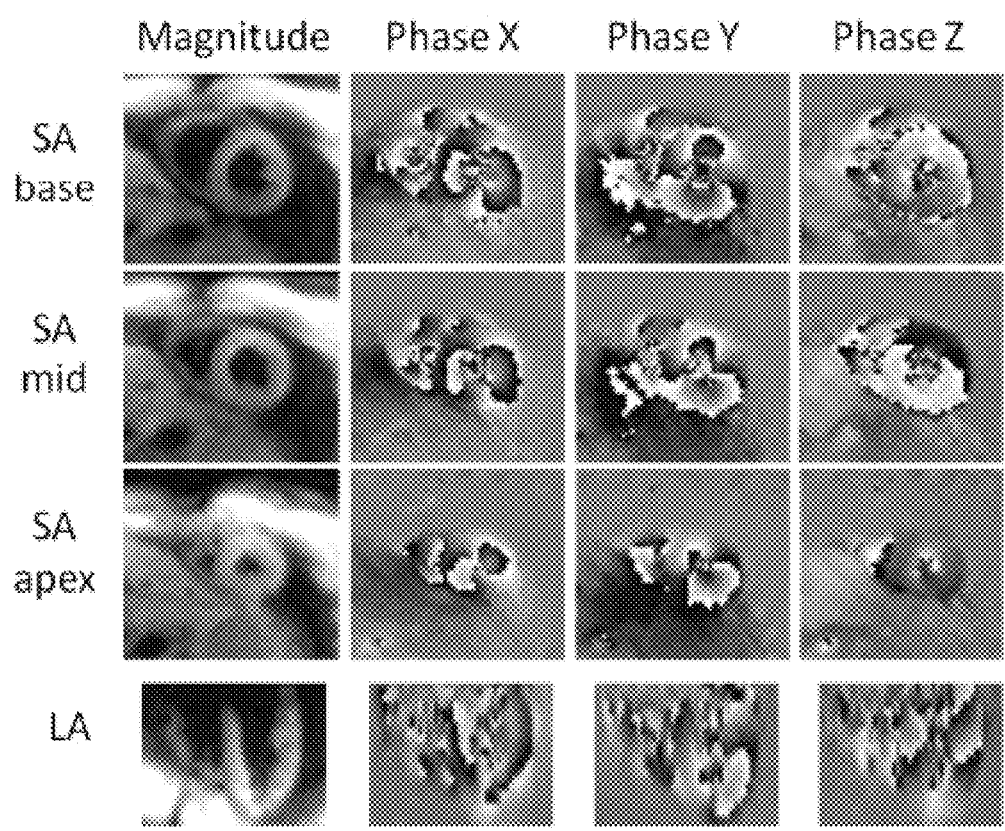
FIG. 9 shows CS-accelerated 3D cine DENSE images. Three short-axis (SA) views at base, mid and apex locations, along with one long axis (LA) view are shown in different rows.
Figure 10:
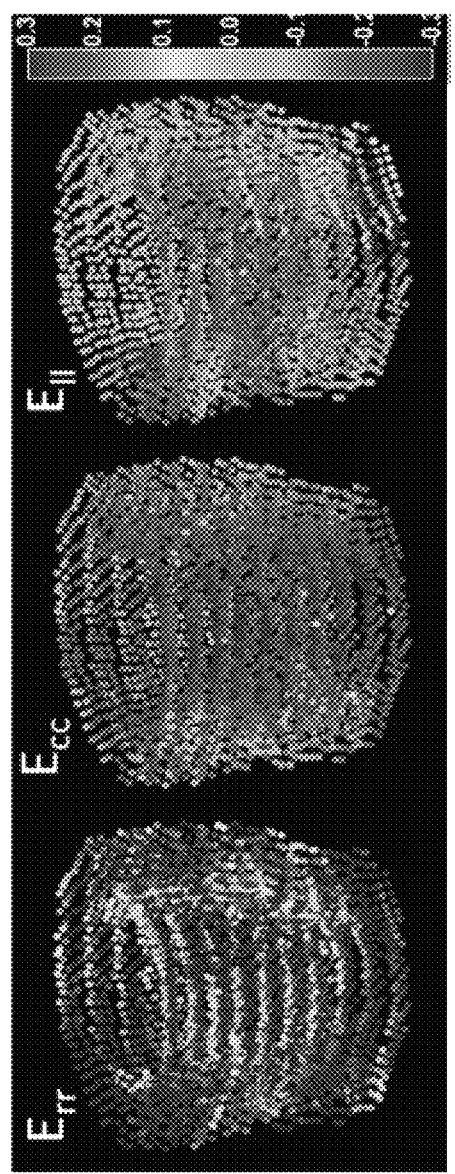
FIG. 10 shows 3D voxel-wise strain maps of a left ventricle (LV) at end systole. Radial ($E_{rr}$), circumferential ($E_{cc}$) and longitudinal strain ($E_{ll}$) maps show values in the range of normal subjects.

Example reconstructed images from rate-6 prospectively accelerated 3D DENSE data show high image quality in both magnitude and phase through the whole heart (FIG. 9). In FIG. 9, three shortaxis (SA) views at base, mid and apex locations, along with one long axis (LA) view are shown in different rows. The magnitude images (col. 1) show clear delineation of the myocardium. All the phase images with displacement encodings in x (col. 2), y (col. 3) and z (col. 4) show clear phase information that can be utilized for strain analysis. The strain analysis (see example voxel-wise strain maps in FIG. 10) obtained from the reconstructed images agreed well with historical strain values ([1]). The average accelerated scan time for all volunteers was 3.0±1.4 minutes with navigation acceptance of 58±28%.

Thus, it is shown by the results in the implementation of aspects of the present disclosure in this Example 2 that accelerated 3D cine DENSE imaging can improve scan time from ~25 minutes to ~3 minutes. High image quality was achieved and strain analysis showed expected values for normal subjects. These results suggest that acceleration can make it feasible to routinely employ 3D cine DENSE for clinical comprehensive myocardial strain imaging with scan times of around 3 minutes.

CONCLUSION

The specific configurations, choice of materials and the size and shape of various elements can be varied according to particular design specifications or constraints requiring a system or method constructed according to the principles of the present disclosure. Such changes are intended to be embraced within the scope of the present disclosure. The presently disclosed embodiments, therefore, are considered in all respects to be illustrative and not restrictive. The scope of the present invention is indicated by the appended claims, rather than the foregoing description, and all changes that come within the meaning and range of equivalents thereof are intended to be embraced therein.

LIST OF REFERENCES

[1] Simpson, R. M. et al., JMRI 2013; 37(3): 576-599.
[2] Spottiswoode, B. S. et al., Med. Image Anal. 2009; 13(1): 105-115.
[3] Young, A. A. et al., Magnetic Resonance in Medicine, 67(6): 1590-1599 (2012).
[4] Candes, J. et al., "An Introduction to Compressive Sampling". IEEE Signal Processing Magazine, March 2008, p. 22.
[5] Clarke, G. "Parallel Imaging: Techniques, Quality Control, and Applications" (presentation). American Association of Physicists in Medicine, Annual Meeting 2007.
[6] Chen, X. et al., "Motion-Compensated Compressed Sensing for Dynamic Contrast-Enhanced MRI Using Regional Spatiotemporal Sparsity and Region Tracking: Block LOw-rank Sparsity with Motion-guidance (BLOSM). Magnetic Resonance in Medicine, 72(4): 1028-1038 (2013).
[7] U.S. Patent Application Publication No. 2014/0219531.
[8] Pruessman, K. et al., "SENSE: Sensitivity Encoding for Fast MRI". Magnetic Resonance in Medicine, 42: 952-962 (1999).
[9] Fessler et al., IEEE Trans. Sign. Proc. 2003; 51(2): 560-74.
[10] Chen, X. et al., JCMR 2014; 16(Supp 1):W16.
[11] Zhong, X. D. et al., "Imaging Three-Dimensional Myocardial Mechanics Using Navigator-gated Volumetric Spiral Cine DENSE MRI". Magnetic Resonance in Medicine, 64(4): 1089-1097 (2010).
[12] Auger, D. et al., JCMR 2014; 16(1):8.

What is claimed is:

1. A method for accelerated imaging of an area of interest of a subject, comprising:
    acquiring magnetic resonance data associated with a physiological activity in an area of interest of a subject, wherein the acquiring comprises performing accelerated variable-density sampling with phase-contrast displacement encoding; and
    reconstructing, from the acquired magnetic resonance data, images corresponding to the physiological activity in the area of interest, wherein the reconstructing comprises performing parallel imaging and compressed sensing.

2. The method of claim 1, wherein the variable-density sampling comprises variable-density spiral sampling.

3. The method of claim 1, wherein the phase-contrast displacement encoding comprises cine displacement encoding with stimulated echoes (DENSE).

4. The method of claim 1, wherein the parallel imaging comprises combining multi-channel parallel imaging data using sensitivity maps calculated from temporally-averaged data.

5. The method of claim 1, wherein the compressed sensing comprises regional-sparsity based compressed sensing.

6. The method of claim 1, wherein the compressed sensing comprises performing motion-guided compressed sensing functions wherein three-dimensional images from the parallel imaging are divided into cubes that are motion-tracked over time and low-rank sparsity is exploited inside the motion-tracked cubes to remove artifacts.

7. A system for accelerated imaging of an area of interest of a subject, comprising:

a magnetic resonance imaging (MRI) device configured to acquire magnetic resonance data associated with a physiological activity in an area of interest of a subject, wherein the acquiring comprises performing, using the MRI device, accelerated variable-density sampling with phase-contrast displacement encoding; and an image processing device coupled to the MM device and configured to reconstruct, from the acquired magnetic resonance data, images corresponding to the physiological activity in the area of interest, wherein the reconstructing comprises performing parallel imaging and compressed sensing.

8. The system of claim 7, wherein the variable-density sampling comprises variable-density spiral sampling.

9. The system of claim 7, wherein the phase-contrast displacement encoding comprises cine displacement encoding with stimulated echoes (DENSE).

10. The system of claim 7, wherein the parallel imaging comprises combining multi-channel parallel imaging data using sensitivity maps calculated from temporally-averaged data.

11. The system of claim 7, wherein the compressed sensing comprises regional-sparsity based compressed sensing.

12. The system of claim 7, wherein the compressed sensing comprises performing motion-guided compressed sensing functions wherein three-dimensional images from the parallel imaging are divided into cubes that are motion-tracked over time and low-rank sparsity is exploited inside the motion-tracked cubes to remove artifacts.

13. A non-transitory computer-readable medium storing instructions that, when executed by one or more processors, cause a system to perform functions for accelerated imaging of an area of interest of a subject, wherein the functions performed include:

acquiring magnetic resonance data associated with a physiological activity in an area of interest of a subject, wherein the acquiring comprises performing accelerated variable-density sampling with phase-contrast displacement encoding; and reconstructing, from the acquired magnetic resonance data, images corresponding to the physiological activity in the area of interest, wherein the reconstructing comprises performing parallel imaging and compressed sensing.

14. The computer-readable medium of claim 13, wherein the variable-density sampling comprises variable-density spiral sampling.

15. The computer-readable medium of claim 13, wherein the phase-contrast displacement encoding comprises cine displacement encoding with stimulated echoes (DENSE).

16. The computer-readable medium of claim 13, wherein the parallel imaging comprises combining multi-channel parallel imaging data using sensitivity maps calculated from temporally-averaged data.

17. The computer-readable medium of claim 13, wherein the compressed sensing comprises regional-sparsity based compressed sensing.

18. The computer-readable medium of claim 13, wherein the compressed sensing comprises performing motion-guided compressed sensing functions wherein three-dimensional images from the parallel imaging are divided into cubes that are motion-tracked over time and low-rank sparsity is exploited inside the motion-tracked cubes to remove artifacts.

* * * * *

UNITED STATES PATENT AND TRADEMARK OFFICE
CERTIFICATE OF CORRECTION

PATENT NO. : 10,143,384 B2
APPLICATION NO. : 14/677905
DATED : December 4, 2018
INVENTOR(S) : Xiao Chen et al.

Page 1 of 1

It is certified that error appears in the above-identified patent and that said Letters Patent is hereby corrected as shown below:

In the Claims

In Claim 7 at Column 15, Line 12, the term "MM" should read --MRI--.

Signed and Sealed this
Twelfth Day of March, 2019

Andrei Iancu
*Director of the United States Patent and Trademark Office*